(12) United States Patent
Piccinelli et al.

(10) Patent No.: US 7,408,077 B2
(45) Date of Patent: Aug. 5, 2008

(54) PERMANENT SURFACE MODIFIERS

(75) Inventors: Piero Piccinelli, Sasso Marconi (IT);
Manuele Vitali, Bologna (IT); Andrea Landuzzi, Bologna (IT); Giovanni Da Roit, Sasso Marconi (IT); Primo Carrozza, Verona (IT); Markus Grob, Riehen (CH); Nicola Lelli, New York, NY (US)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 111 days.

(21) Appl. No.: 10/469,890

(22) PCT Filed: Feb. 28, 2002

(86) PCT No.: PCT/EP02/02149

§ 371 (c)(1),
(2), (4) Date: Apr. 2, 2004

(87) PCT Pub. No.: WO02/072530

PCT Pub. Date: Sep. 19, 2002

(65) Prior Publication Data

US 2004/0162431 A1    Aug. 19, 2004

(30) Foreign Application Priority Data

Mar. 9, 2001  (EP) .................................. 01810244

(51) Int. Cl.
*C07C 69/76* (2006.01)
(52) U.S. Cl. .............................. 560/91; 560/89; 560/90; 560/76; 560/64
(58) Field of Classification Search ................. 562/496, 562/465, 480, 493; 568/308; 560/55, 60, 560/61, 76, 81, 89, 90, 91, 103, 105, 112
See application file for complete search history.

(56) References Cited

U.S. PATENT DOCUMENTS

| | | | | |
|---|---|---|---|---|
| 3,739,015 A | * | 6/1973 | Wattanabe et al. | 560/55 |
| 4,338,322 A | * | 7/1982 | Sato | 514/344 |
| 4,348,399 A | | 9/1982 | Shepherd | 424/263 |
| 5,262,233 A | | 11/1993 | Sudo et al. | 428/327 |
| 5,650,456 A | | 7/1997 | Yun et al. | 524/110 |

FOREIGN PATENT DOCUMENTS

| | | | |
|---|---|---|---|
| EP | 0093968 | | 11/1983 |
| EP | 0897916 | | 2/1999 |
| GB | 1182443 | | 2/1970 |
| GB | 1246236 | * | 9/1971 |
| JP | 4928743 | * | 7/1974 |
| JP | 07330680 | * | 12/1995 |

OTHER PUBLICATIONS

Dellagreca et al., Natural Product Letters (1998), 12(4), 263-270.*

H. Zweifel, Plastics Additives Handbook, 5th Ed., (2001), pp. 609-626.
Patent Abstracts of Japan Publication No. 07330673, Publication Date: Dec. 19, 1995.
Patent Abstracts of Japan Publication No. 07330680, Publication Date: Dec. 19, 1995.
H.-J. Christau et al., Heteroatom Chemistry, vol. 3, No. 4, (No Month Listed/1992), pp. 415-422.
A. F. Artamonov et al., Chemistry of Natural Compounds, vol. 33, No. 5, (Jan. 2, 1997), pp. 571-573.
C. Nourary et al., J. Photochem. Photobiol. A: Chem., vol. 84, (Apr. 28, 1994), pp. 317-326.

* cited by examiner

*Primary Examiner*—Karl J Puttlitz
(74) *Attorney, Agent, or Firm*—Tyler A. Stevenson

(57) ABSTRACT

The invention relates to novel compounds of the formula I, II; III or IV wherein the general symbols are as defined in claim 1. These compounds are useful as surface modifiers for polymers in order to improve resistance to fog formation or water and oil repellency.

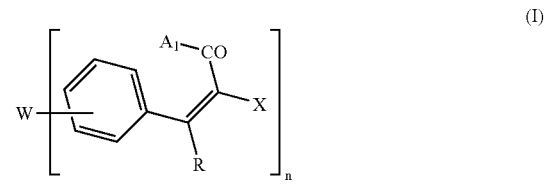

(I)

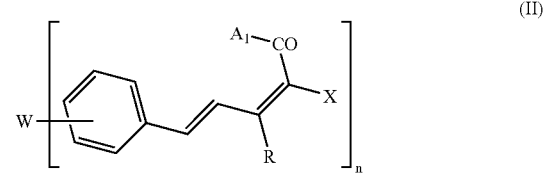

(II)

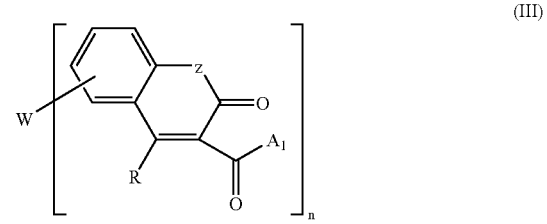

(III)

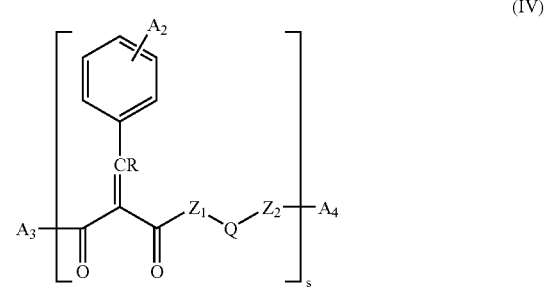

(IV)

5 Claims, No Drawings

PERMANENT SURFACE MODIFIERS

This invention relates to novel compounds suitable for olefin polymer compositions which are resistant to fogging or show water and oil repellency, especially when employed as a packaging film for moist products and as a greenhouse film for agricultural applications.

Agricultural films which are largely used in greenhouse culture or tunnel culture chiefly include soft ethylene resin films which are about 20 to 250 microns thick and which comprise, as a base resin, polyvinyl chloride, branched low-density polyethylene (LDPE), ethylene-vinyl acetate copolymers (EVA), linear low-density polyethylene (LLPDE), etc. Of the various properties required for the agricultural films, particularly important are weather resistance, anti-fogging properties, heat-retaining properties, and transparency. To cope with the recent situation confronting agriculture such as an increased cost and a shortage of labour, development of films having an extended duration of life before re-placement is desired.

The atmosphere within greenhouses or tunnels surrounded by an agricultural film is saturated with water vapour which evaporates from the soil or plants, and the water vapour drop-wise condenses on the inner surface of a cold film to cause fogging. Water droplets on the film not only greatly reduce the incident sunlight due to irregular reflection but the droplets fall on the plants resulting in frequent occurrence of diseases.

Another problem closely related to the above discussed greenhouse problem applies to so-called food packaging films when food, e. g. meat products, are packaged on trays and over wrapped with a plastic film at room temperature. When these packages are placed in a refrigerator at around 4° C., the air enclosed in the package cools and is no longer able to hold its water in the vapour phase. The air in the package becomes saturated and the water condenses as water droplets onto the film's surface.

To overcome these problems, polymer films are modified with antifogging additives. The modified plastic films do not prevent the formation of condensation per se. However, while water vapour condenses on such films, antifogging additives migrate to the surface of the film, causing the condensate to spread evenly over the film's surface and run off instead of forming droplets, cf. Plastics Additives Handbook, 5th Edition 2001, Hans Zweifel Ed., Hanser Publisher sMunich, Hanser Gardner Publications, Inc. Cincinnati, pages 609-626.

Representative antifogging additives are glycerol monooleate, polyglycerol esters, sorbitan esters, ethoxylated sorbitan esters, nonylphenol ethoxylate or ethoxylated alcohols. As representative state of the art U.S. Pat. No. 5,262,233 is cited, which discloses the incorporation of polyethylene oxide alkyl ethers as non-ionic surfactants in agricultural polymeric films.

Antifogging additives can be incorporated within the polymer matrix as pure additives or as masterbatches or concentrates. Typical antifogging additive concentrations range between 1 and 3%. The additives have the property of migrating to the surface of the film. In a monolayer film, the anti-fogging additive migrates in both directions, towards the inside of the agricultural film where the antifogging effect is desirable, but also to the outside of the film where it is unnecessary. On the outside of the polymer film, antifogging additive is lost as it is washed off by rain.

Antifogging additives can also be applied to the surface by coating. Surfactant molecules coatings have the undesirable property of forming a weak attachment to polymeric films or foils, particularly polyethylene films and are washed away by the action of heat and humidity.

However, an anti-fogging film obtained by coating a soft plastic film with an anti-fogging agent has not yet been employed extensively as an agricultural film for the following reasons. Because of their low surface energy, soft plastic films for agricultural use generally have poor wettability and adhesion when coated with surface active agents or hydrophilic high polymeric substances which have been used as anti-fogging agents. This tendency is particularly conspicuous with soft ethylene resin films of low polarity, e.g., LDPE, EVA, and LLDPE films. Therefore, where an anti-fogging agent is spray coated with a power atomiser onto a soft ethylene resin film, the anti-fogging agent needs to be used in a large quantity and this increases cost, and a large amount of time is required for spray coating operation. Further, spray coating cannot be effected uniformly with insufficient anti-fogging effects arising. Where an anti-fogging agent is applied using a coater, etc., a large quantity of a coating is consumed, and the coating speed cannot be increased, resulting in an increase of cost. In either case, the coated anti-fogging agent is washed away together with running water droplets due to poor adhesion resulting in a very short life for the ant-fogging properties. Furthermore, the coated film undergoes blocking due to the stickiness of the anti-fogging agent. As a result, it has been impossible to retain anti-fogging effects in a stable manner for a long duration of at least one year, more desirably, several years. Most of the state-of-the-art agricultural films exhibit anti-fogging properties from coated additives, for a period of only about one month.

Anti-fogging agents commonly incorporated into the films include non-ionic, anionic and cationic surface active agents.

Other methods for providing anti-fogging properties to agricultural films, in addition to the coating method and incorporation method, include chemical modification of the ethylene base resin or the ethylene resin film surface by introducing a polar group, such as a hydrophilic group. This technique, however, entails high cost at the present time and is difficult to apply to agricultural films.

Suitable inorganic hydrophilic colloidal substances include colloidal silica, colloidal alumina, colloidal $Fe(OH)_2$, colloidal $Sn(OH)_4$, colloidal $TiO_2$, colloidal $BaSO_4$, and colloidal lithium silicate, with colloidal silica and colloidal alumina most generally used. Suitable hydrophilic organic compounds include various non-ionic, anionic or cationic surface active agents; graft copolymers mainly comprising a hydroxyl-containing vinyl monomer unit and from 0.1 to 40% by weight of a carboxyl-containing vinyl monomer unit or a partial or complete neutralisation product thereof; and sulpha-containing polyester resins.

There is still a need for polyolefin-based films having long lasting anti-fogging properties.

One way to obtain "permanent" additives is to covalently bond them to the polymeric matrix through a chemical reaction. Among possible reactions, one option is to have photo-reactive moieties in the additive molecule so that, by exposition to visible and/or ultraviolet light, either from an artificial source or from solar irradiation, the molecule reacts with the polymeric substrate. As a consequence, the additive results to be grafted to the polymer, so that the effect imparted by the former is permanent. Several examples of photo-reactive additives are reported in the literature, for example in EP-A-0 897 916.

It has surprisingly been found that combining opportunely migration of anti-fogging agents to the surface of the polymer substrate with the reaction of a photo-sensible moiety contained in the anti-fogging additive itself, it is possible to have the reaction induced by light when most or at least part of the additive is at the surface of the plastic film. This results in long-term ant-fogging properties, because the additive is permanently bound to the polymer and cannot be physically removed.

Another option is to apply the anti-fogging additive to the surface by coating (e.g. by spraying or by roller-coating) and, after that, induce the reaction between the photo-graftable part of the additive and the polymer either by a proper artificial treatment or by directly exposing the plastic film to the solar light. In this case the reaction must be fast enough, in order to occur before the additive is washed off by humidity. Similar to the previous example, the anti-fogging effect is then retained for a long time.

Of interest are also properties other than fogging resistance. Water repellency and oil repellency in particular are the relevant properties in this context. The former can reduce dust deposition, through mechanical removal of water rapidly flowing along the repellent polymer surface and may find application in greenhouse films for agriculture application, in order to enhance light transmittance inside the greenhouse. Oil repellency has the consequence to impart stain resistance to fabrics made of fibers or non woven.

Object of the invention is a compound of the formula I, II III or IV

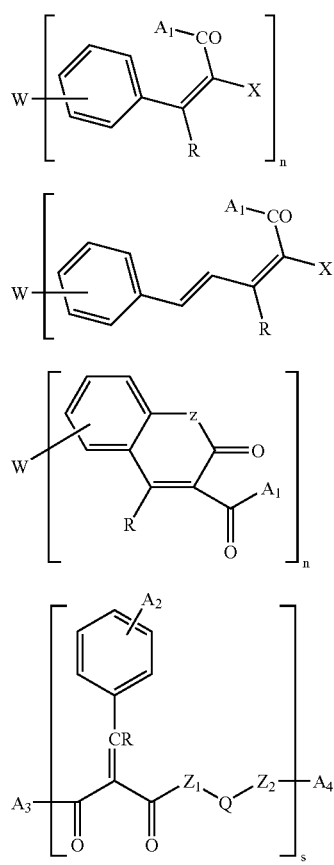

wherein,
$A_1$ is a residue selected from the group consisting of polyol, sorbitol, sorbitane, glycerol, diglycerol, polyglycerol, ethoxylated and/or propoxylated glycerol, ethoxylated and/or propoxylated sorbitane, hydroxy $C_1$-$C_4$alkylamine, a polyoxyalkylene ether residue of the formula —O—[—$CHR_1$—$(CH_2)_r$O]$_q$—$CHR_1$—$(CH_2)_r$—$OR_2$ or a residue of the formula —O—[—$CHR_1$—$(CH_2)_r$]$_g$—$(CF_2)_j$—$CF_3$, wherein
  $R_1$ is hydrogen or $C_1$-$C_4$alkyl,
  $R_2$ is $C_1$-$C_{20}$alkyl,
  g is from 0 to 5,
  j is from 1 to 20,
  r is 1, 2, 3 or 4,
  q is from 1 to 100,
X is hydrogen, CN, —C(O)$R_3$, —C(O)$OR_4$, —C(O)$A_1$, wherein
  $R_3$ and $R_4$ each independently are hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl,
R is hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl,
Z is O, S or $NR_5$ wherein
  $R_5$ is hydrogen, $C_1$-$C_{20}$alkyl or $C_1$-$C_{20}$hydroxyalkyl,
W is an organic radical of valency equal to n,
n is 1, 2, 3 or 4,
$A_2$ is hydrogen, $OR_6$—$NR_7R_8$, —$SR_9$, —$OCH_2C(O)$-$A_1$ or —$C(O)$-$A_1$, wherein
  $R_6$, $R_7$, $R_8$, $R_9$ each independently are hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl,
$A_3$ is $C_1$-$C_6$alkoxy,
$A_4$ is H, $C_1$-$C_6$alkyl,
Q is —$CH_2$—$CH_2$—$(NR_{10})$—$CH_2$—$CH_2$—, —$(CHR_{11}$-$CH_2)_p$—, —$CR_{11}H$—$CH_2$—O—$(CHR_{11}$—$CH_2$—O—$)_p$—$CHR_{11}$—$CH_2$—, wherein
  $R_{10}$ is hydrogen, $C_1$-$C_{20}$alkyl, $C_1$-$C_{20}$hydroxyalkyl,
  $R_{11}$ is hydrogen or $C_1$-$C_4$alkyl,
  p is from 1 to 100,
$Z_1$ and $Z_2$ each independently are O, S or $NR_{12}$ wherein
  $R_{12}$ is hydrogen, $C_1$-$C_{20}$alkyl, $C_1$-$C_{20}$hydroxyalkyl, and
s is from 2 to 50.

Of special interest are compounds of formula I, II, III or IV, wherein
$A_1$ is a residue selected from the group consisting of polyol, sorbitol, sorbitane, glycerol, diglycerol, polyglycerol, ethoxylated and/or propoxylated glycerol, ethoxylated and/or propoxylated sorbitane, hydroxy $C_1$-$C_4$alkylamine or a polyoxyalkylene ether residue of the formula —O—[—$CHR_1$—$(CH_2)_r$O]$_q$—$CHR_1$—$(CH_2)_r$—$OR_2$ wherein
  $R_1$ is hydrogen or $C_1$-$C_4$alkyl,
  $R_2$ is $C_1$-$C_{20}$alkyl,
  r is 1, 2, 3 or 4,
  q is from 1 to 100,
X is hydrogen, CN, —C(O)$R_3$, —C(O)$OR_4$, —C(O)$A_1$, wherein
  $R_3$ and $R_4$ each independently are hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl,
R is hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl,
Z is O, S or $NR_5$ wherein
  $R_5$ is hydrogen, $C_1$-$C_{20}$alkyl or $C_1$-$C_{20}$hydroxyalkyl,
W is an organic radical of valency equal to n,
n is 1, 2, 3 or 4,
$A_2$ is hydrogen, $OR_6$—$NR_7R_8$, —$SR_9$, —$OCH_2C(O)$-$A_1$ or —$C(O)$-$A_1$, wherein
  $R_6$, $R_7$, $R_8$, $R_9$ each independently are hydrogen, $C_1$-$C_{20}$alkyl, $C_1$-$C_{20}$hydroxyalkyl, $C_5$-$C_8$cycloalkyl, $C_2$-$C_{20}$alkenyl, $C_2$-$C_{20}$alkynyl or $C_6$-$C_{20}$aryl, $A_3$ is $C_1$-$C_6$alkoxy,
$A_4$ is H, $C_1$-$C_6$alkyl,
Q is —$CH_2$—$CH_2$—($NR_{10}$)—$CH_2$—$CH_2$—, —($CHR_{11}$—$CH_2$)$_p$—, —$CR_{11}$H—$CH_2$—O—($CHR_{11}$—$CH_2$—O—)$_p$—$CHR_{11}$—$CH_2$—, wherein
  $R_{10}$ is hydrogen, $C_1$-$C_{20}$alkyl, $C_1$-$C_{20}$hydroxyalkyl,
  $R_{11}$ is hydrogen or $C_1$-$C_4$alkyl,
  p is from 1 to 100,
$Z_1$ and $Z_2$ each independently are O, S or $NR_{12}$ wherein
  $R_{12}$ is hydrogen, $C_1$-$C_{20}$alkyl, $C_1$-$C_{20}$hydroxyalkyl, and
s is from 2 to 50.

When n is 2,3 or 4 each of the radical $A_1$, X, R, Z can have the same or a different meaning in the units of the formulae I,II or III. Thus, the organic radical W can be as follows:
when n is 1, W is $A_2$ as defined in claim 1;
when n is 2, W is —O-(Q)-O—,—($R_{13}$)N-(Q)-N($R_{14}$)—, —S-(Q)-S—, —OC(O)-(Q)-C(O)O—, —OC(S)-(Q)-C(S)O—, —NC(O)-(Q)-C(O)N—, wherein
  Q is as defined in claim 1,
  $R_{13}$ and $R_{14}$ each independently are hydrogen, $C_1$-$C_{20}$alkyl or $C_1$-$C_{20}$hydroxyalkyl,
when n is 3, W is a trivalent residue of the formula

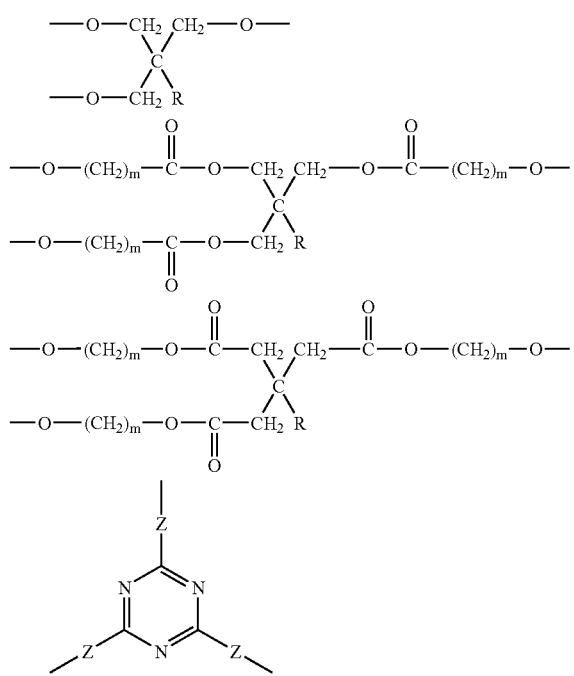

with R and Z as defined in claim 1 and m is 1 to 6
when n is 4, W is a tetravalent residue of the formula

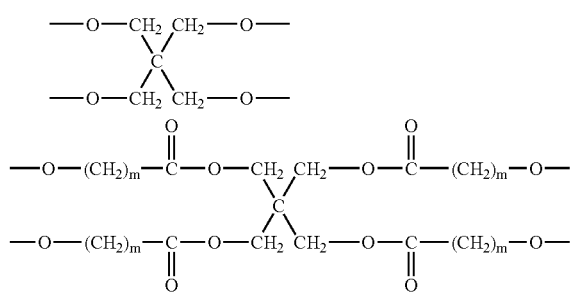

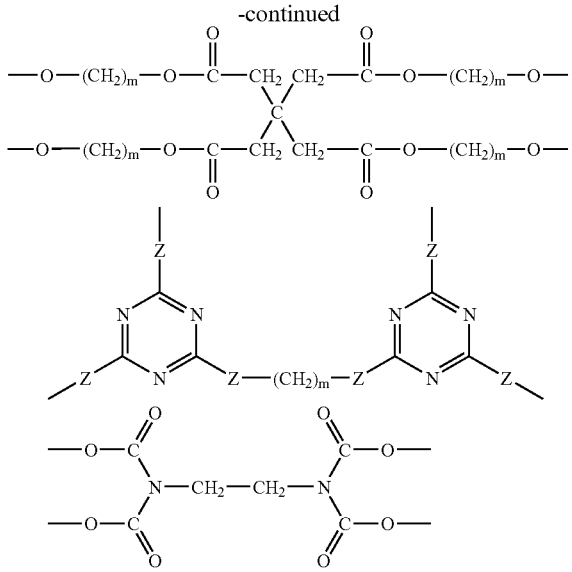

with Z as defined above and m is 1 to 6.

The term "alkyl" by itself or as part of another substituent means, a straight or branched chain monovalent hydrocarbon radical such as methyl, ethyl, n-propyl, isopropyl, n-butyl, tertiary butyl, isobutyl, sec-butyl, tert butyl, n-pentyl, isopentyl, neopentyl, heptyl, hexyl, 2-ethylhexyl, octyl, nonyl, decyl, undecyl, dodecyl, tridecyl, tetradecyl, hexadecyl, octadecyl and the like. The term "alkyl" includes $C_1$-$C_4$alkyl, $C_1$-$C_6$alkyl, $C_1$-$C_{20}$alkyl.

The term "alkenyl", as used herein, represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" as used herein, represents such radicals as ethynyl, propynyl, butynyl, pentynyl, hexynyl, or heptynyl.

The term "hydroxyalkyl", as used herein, represents alkyl radicals having one or more hydroxy substituents.

The term "$C_6$-$C_{20}$ aryl", as used herein, represents phenyl, naphthyl, phenantrenyl, fluorenyl, perilenyl.

The term "polyol", as used herein, refers to alcohols containing two or more hydroxyl groups and includes for example ethylene glycol, diethylene glycol, triethylene glycol, propylene glycol, dipropylene glycol, 1,3-propane diol, 2-($C_1$-$C_4$alkyl)propane 1,3-diol, 1,4-butane diol, 1,5-pentane diol, 1,6-hexane diol and neopentyl glycol.

The term "polyglycerol", as used herein, refers to molecules having from 3 to 30 glycerol units per molecule.

The term "hydroxy $C_1$-$C_4$alkylamine", as used herein, includes for example ethanolamine, diethanolamine, tri-ethanolamine, isopropanolamine, di-isopropanolamine, tri-isopropanolamine, tris-(hydroxymethyl)amino methane and the like.

Concerning the compounds of the formula I, II or III, those are preferred wherein n is 1.

Especially preferred are those wherein
n is 1,
W is hydrogen or $C_1$-$C_{20}$alkoxy,
$A_1$ is a polyoxyalkylene ether residue of the formula —O—[—$CH_2$—$CH_2$—O]$_q$—$CH_2$—$CH_2$—$OR_{11}$, wherein q is from 4 to 30; —O—CH$_2$—CH$_2$—(CF$_2$)$_j$—CF$_3$, wherein j is from 3 to 8; a glycerol residue or a sorbitane residue, X is —C(O)A$_1$,
Z is O, and
R is hydrogen.

Concerning the compounds of formula IV, those are preferred wherein
s is from 5 to 10,
A$_2$ is hydrogen or C$_1$-C$_{20}$alkoxy,
Z$_1$ and Z$_2$ are O,
Q is —CH$_2$—CH$_2$—O—(CH$_2$—CH$_2$—O)p-CH$_2$—CH$_2$—,
p is from 4 to 30,
R is hydrogen,
A$_3$ is OC$_2$H$_5$,
A$_4$ is hydrogen.

The compounds of the present invention are suitable for a permanent surface modification including grafting, especially of hydrophobic polymers like polyolefins, via photoreactive groups. The compounds are graftable functional monomers having in addition a hydrophilic residue. They are preferably used as antifog agents for greenhouse films.

The compound of formula I, II III or IV can be prepared using known methods of the organic chemistry or in analogy to these methods.

Compounds of the formula I can be prepared for example according to the following scheme

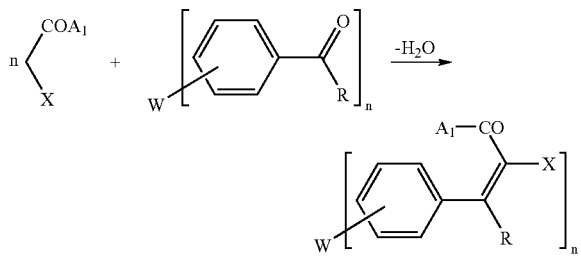

A benzaldehyde derivative is for example condensed with a malonic acid derivative according to a conventional alkylation reaction, in the presence of a base such, for example, piperidine, piperazine, in an inert solvent. The reaction can, for example, be carried out in aromatic solvents such as toluene or xylene. The reaction is preferably carried out at from 50° C. to the boiling point of the reaction mixture, preferably under reflux conditions. The pressure is preferably atmospheric pressure.

The benzaldehyde derivatives suitable for use as starting materials are commercially available or can be prepared by techniques well known to those skilled in the art.

When starting with a malonic acid diester, the final product is obtained advantageously by a transesterification reaction. The transesterification reaction is promoted by heating the reactants generally within the range of from about 100° C. to 200° C., preferably 150-180° C. in the presence of a transesterification catalysts such as for example an organotin catalysts, preferably dibutyltin oxide. Other known transesterfication catalysts can also be used.

The compounds of formula II can be prepared for example as described above starting from a cinnamaldehyde derivative.

The compounds of formula III can be prepared for example by transesterfication of commercially available 2H-1-benzopyran-3-carboxylic acid-2-oxo-ethylester or according to the following reaction scheme:

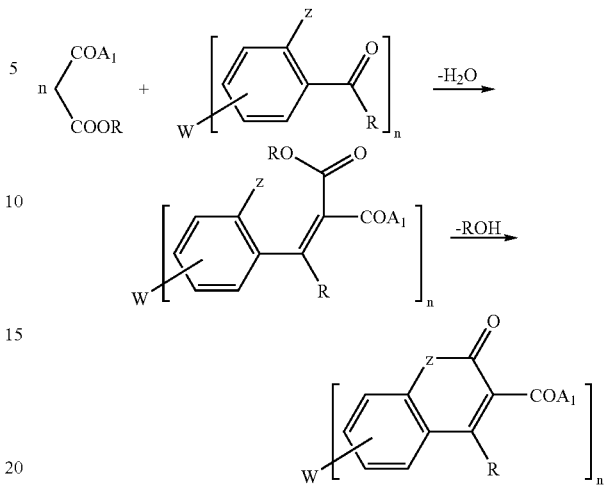

The compounds of the formula IV can be obtained for example by polymerisation of a benzylidene malonic ester derivative with a polyoxyalkylene compound.

Another embodiment of the invention are compositions comprising
a) a polymer or mixtures of polymers and,
b) as additive for surface modification, at least one compound of the formula I III, III or IV or mixtures thereof.

Preferred is a composition comprising polymers or mixtures of polymers and, as additive for surface modification, at least one compound of the formula I, II or III, wherein n is 1.

Especially preferred are compositions comprising polymers or mixtures of polymers and, as additive for surface modification, at least one compound of the formula I, II or III, wherein
n is 1,
W is hydrogen or C$_1$-C$_{20}$alkoxy,
A$_1$ is a polyoxyalkylene ether residue of the formula —O—[—CH$_2$—CH$_2$—O]$_q$—CH$_2$—CH$_2$—OR$_{11}$, wherein q is from 4 to 30; —O—CH$_2$—CH$_2$—(CF$_2$)$_j$—CF$_3$, wherein j is from 3 to 8; a glycerol residue or a sorbitane residue,
X is —C(O)A$_1$,
Z is O, and
R is hydrogen.

Also preferred are compositions comprising polymers or mixtures of polymers and, as additive for surface modification, at least one compound of the formula IV, wherein
s is from 5 to 10
A$_2$ is hydrogen or C$_1$-C$_{20}$alkoxy,
Z$_1$ and Z$_2$ are O,
Q is —CH$_2$—CH$_2$—O—(CH$_2$—CH$_2$—O)p-CH$_2$—CH$_2$—
p is from 4 to 30,
R is hydrogen,
A$_3$ is OC$_2$H$_5$
A$_4$ is hydrogen.

Polymers or mixtures of such polymers are especially thermoplastic polymers such as polyolefins, especially polyethylene and polypropylene; polyester and polycarbonates.

In general the compounds of the formula I, II, III or IV or mixtures thereof are added to the material to be stabilised in amounts of from 0.01 to 10%, preferably 0.01 to 5%, in particular from 0.05 to 5% based on the weight of component (a) to be stabilised. Particular preference is given to the use of the novel compounds in amounts of from 0.5 to 3%, especially from 1 to 3%.

The polyolefins or olefin copolymers are mainly the materials listed below:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
 a) radical polymerisaton (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-i-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(αmethylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatc, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatine and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Novel polymer compositions can be employed in various forms and/or processed to give various products, for example as films, sheets, fibres, tapes, moulding compositions, profiles, or as binders for coating materials, adhesives or putties. Preferred are films and sheets.

Incorporation of the compounds of the formula I, II, III or IV or mixtures thereof into the polymers can be effected, for example, by mixing in or applying the compounds of the formula I, II, III or IV or mixtures thereof, and, if desired, further additives by the methods which are customary in the art.

Incorporation can take place prior to or during the shaping operation, or by applying the dissolved or dispersed compound to the polymer, with or without subsequent evaporation of the solvent.

The compounds of the formula I, II, III or IV or mixtures thereof can be incorporated by the following methods:

as emulsion or dispersion (e.g. to emulsion polymers),
as a dry mixture during the mixing in of additional components,
by direct introduction into the processing apparatus (e.g. extruders, internal mixers, etc.),
by surface application for example by topical spraying, roller coating or solvent casting.

The obtained composition undergoes photografting via exposition under natural light or artificial suitable UV source.

According to the use the photografting can be achieved after the setting of the films or sheets on the final destination by the effect of natural light (e.g. greenhouses) or, immediately after film or sheet extrusion under UV source, placed along the working line or in a separate moment.

A further subject of the invention is the use of a compound of the formula I, II, III or IV or mixtures thereof as graftable surface modifiers applied as bulk additive in the range of 0.5-10%, in the polymers formulation.

The compound of the formula I, II, III or IV or mixtures thereof can be applied topically on the interested surface via spraying or roller coating in the range of 0.1-3% based on polymer quantity.

The photografting is accomplished via sunlight exposition for greenhouse antifog application. or via an artificial photografting under suitable UV light source.

The composition of the invention may contain further additives in addition to the components described above, such as the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulphide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(-α-methylbenzyl)-4-nonylphenol], 2,2'-methylenebis[6-(α,α-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra (5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulphide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tertbutyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tertbutyl/tert-octylphenothiazines, a mixture of mono- and dialkylated tert-octylphenothiazines, N-allylphenothiazine, N,N,N',N'-tetraphenyl-1,4-diaminobut-2-ene.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octloxyphenyl)benzotriazole, 2-(3',5'-di-tert-amyl-2'-hydroxyphenyl)benzotriazole, 2-(3',5'-bis(α,αdimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterificaton product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$—, where R=3'-tert-butyl-4'-hydroxy-5'-2H-benzotriazol-2-ylphenyl, 2-[2'-hydroxy-3'-(α,α dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl-undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-o-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides. 2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethyphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy] phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxy pentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[δ,γ]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[δ,γ]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba-Geigy), tris(nonylphenyl) phosphite,

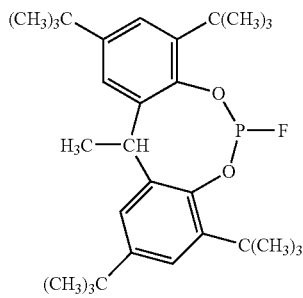
(A)

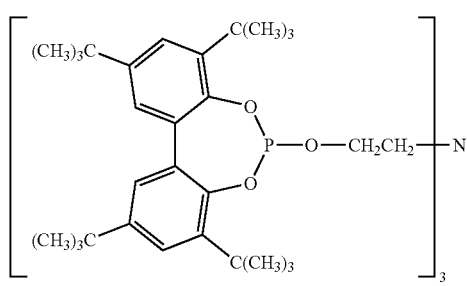
(B)

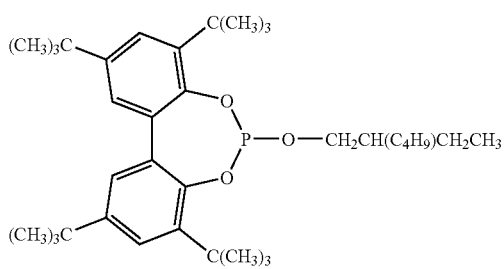
(C)

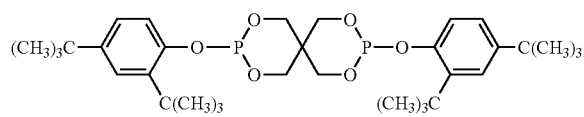
(D)

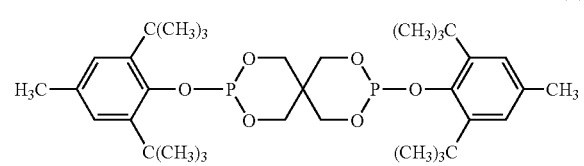
(E)

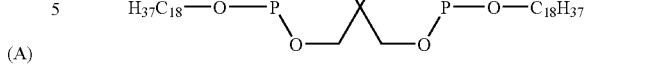
(F)

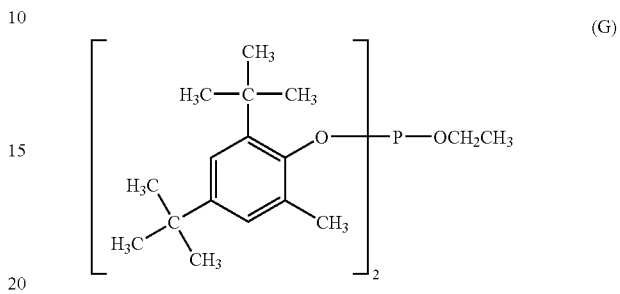
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecyinitrone, N-tetradecyl-alpha-tridecyinitrone, N-hexadecyl-alpha-pentadecylnitrone, N-octadecyl-alpha-heptadecyinitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(p-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyl-dibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

Of interest is the use of the compounds of the formula I, II, III or IV as surface modifiers for polymers in order to improve resistance to fog formation or water and oil repellency.

The present invention also relates to a process for modifying the surface of polymers in order to improve resistance to fog formation or water and oil repellency, which comprises incorporating or applying thereto at least a compound of the formula I, II, III or IV.

The examples below illustrate the invention further. All parts or percentages, in the examples as in the remainder of the description and in the claims, are by weight, unless stated otherwise. Room temperature denotes a temperature in the range 20-30° C., unless stated otherwise. Data given for elemental analysis are in % by weight calculated (cal) or experimentally measured (exp) for the elements C, H and N. In the examples, the following abbreviations are used:

| | |
|---|---|
| % w/w | percent by weight; |
| % w/v | percent weight by volume; x % (w/v) stands for x g solid dissolved in 100 ml liquid; |
| m.p. | melting point or range; |
| PO | polyolefin; |
| PP | polypropylene; |
| LDPE | low density polyethylene; |
| DSC | differential scan calorimetry; |
| NMR | nuclear magnetic resonance (of $^1$H, if not otherwise indicated). |
| GC | Gas Chromatography |
| GPC | Gel Permeation Chromatography |

A: PREPARATION EXAMPLES

Compounds of Formula I

Example A1

Preparation of 2-(4-dodecyloxy-benzylidene)-malonic acid bis-(2,3 dihydroxy-propyl) Ester.

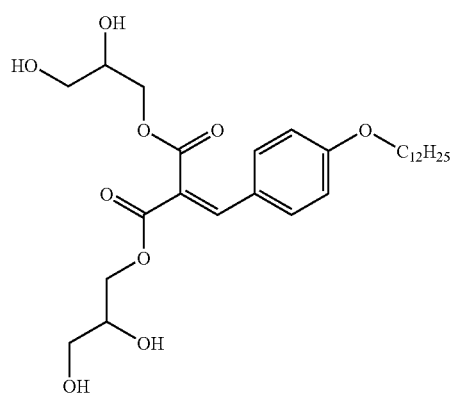

a) Preparation of 4-dodecyloxy-benzaldehyde.

100 g of 4-hydroxy-benzaldehyde are reacted with 224.5 g of dodecyloxybromide along with 56.7 g of anhydrous KOH (85%) in 1 l of 4-methyl-2-hydroxy-pentane. The mixture is then heated to reflux and maintained at reflux for 7 hours. The cooled reaction mixture is filtered to eliminate salts and distilled in a claisen equipment. 184 g (yield 77%) of a clear oil are collected at 178-181° C. and 0.5 mbar, which slowly crystallises on standing at room temperature.

b) Preparation of 2-(4-dodecyloxy-benzylidene)-malonic acid diethyl ester.

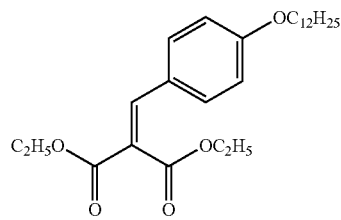

100 g (0.344 mol) of 4dodecyloxy-benzaldehyde [as prepared in step a)], are reacted in 750 ml of toluene with 82.7 g of malonic acid diethyl ester (0.516 mol) and 3 g of piperazine as catalyst for 20 hours in azeotropic reflux. After 10 hours an additional portion of catalyst is added in order to complete the reaction. The reaction mixture is cooled, filtered and washed with water. The clear solution is evaporated under vacuum and the obtained clear oil is crystallised with 95% ethanol. After filtration and drying in oven, 114 g of 2-(4-dodecyloxy-benzylidene)-malonic acid diethyl ester are collected (96% (GC); yield 75%).

c) Preparation of the Title Compound.

50 g of 2-(4-dodecyloxy-benzylidene)-malonic acid diethyl ester [as prepared in step b)] are reacted with 57.4 g of 2,2-dimethyl-1,3-dioxolane-4-methanol (excess 100%) and with 0.5 g of dibutyl tin oxide as catalyst. The reaction mixture is heated at 145-150° C. for 12 hours with distillation of ethanol under mild vacuum. Excess of alcohol is distilled off under stronger vacuum. The obtained raw material is dissolved in toluene, washed with water and filtered. After evaporation of the solvent under vacuum, the resinous mass is crystallised from ethanol (95%). The intermediate filtered ketal (about 48 g, dry) is suspended with fresh ethanol and 26 g of aqueous HCl (6 N) are added. The reaction mass is allowed to react for 24 hours at room temperature under stirring. Solvent is distilled off from the clear solution and the resin is washed in ethyl acetate/water. After evaporation of the solvent, hexane is added and the resin is precipitated with hexane resulting in 41 g of the title product as waxy solid with a melting point of 80-85° C.

Example A2

Preparation of 2-(4-dodecyloxy-benzylidene)-malonic acid bis{2-(3,4 dihydroxy-tetrahydro-furan-2-yl)-2-hydroxy-ethyl}ester

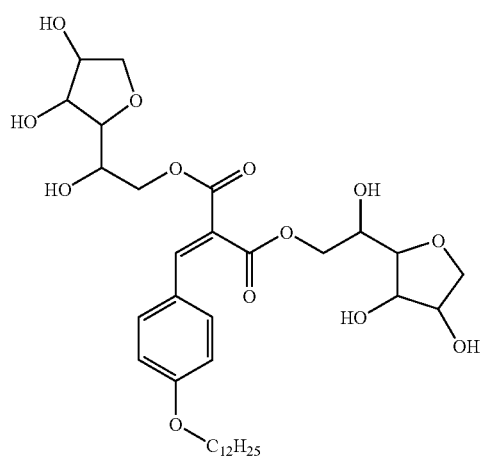

a) Preparation of sorbitane as described in U.S. Pat. No. 4,297,290.

b) Preparation of the Title Compound.

100 g of 2-(4-dodecyloxy-benzylidene)-malonic acid diethyl ester (as prepared in Example A1b) are reacted with 94.7 g of sorbitane (as prepared in step a) and 5 g of dibutyl tin oxide as catalyst in 500 ml of diglyme for 4 hours. Subsequently, the temperature is raised up to 175-180° C. distilling off the solvent, and the mixture is maintained for 10 hours at 175-180° C. Finally, residual solvent is distilled off under vacuum and the cooled reaction mass is dissolved in ethyl acetate and washed with water in order to eliminate the excess of sorbitane. The solvent is distilled off under vacuum. The title compound is obtained as a resinous material (128 g).

Example A3

Preparation of 2-(4-methoxy-benzylidene)-malonic acid bis-(2,3 dihydroxy-propyl) ester

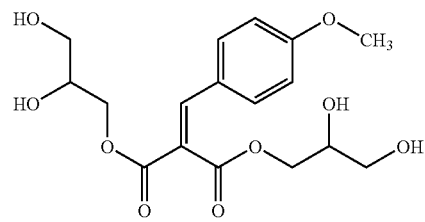

a) Preparation of propanedioic acid, bis[(2,2-dimethyl-1,3-dioxolan-4-yl)methyl] ester.

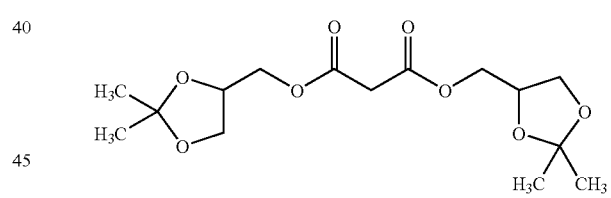

The ester was prepared according to the procedure described in U.S. Pat. No. 4,598,073.

b) Preparation of the Title Compound.

12 g of p-anisaldehyde and 30 g of propanedioic acid bis[(2,2-dimethyl-1,3-dioxolan-4-yl)methyl] [as prepared in step a)] ester are refluxed azeotropically in 300 ml of toluene with 1.5 g of piperazine as catalyst, for 6 hours. The organic phase is cooled, washed with water and the solvent is distilled off. The resulting clear resin is purified through a chromatography column of silica gel using a solution toluene/THF=10/1. 20 g of di-ketal is obtained which is reacted with 200 ml of absolute ethanol and 7.4 g of 6N HCl for 7 hours at ambient temperature. After distillation of the solvent the resin is purified through a chromatography column of silica gel using a solution hexane/THF=⅕. 8 g of a clear resin are obtained.

Example A4

Preparation of 2-(4-dodecyloxy-benzylidene)-malonic acid bis (poly(ethylene glycol) methyl ether)ester

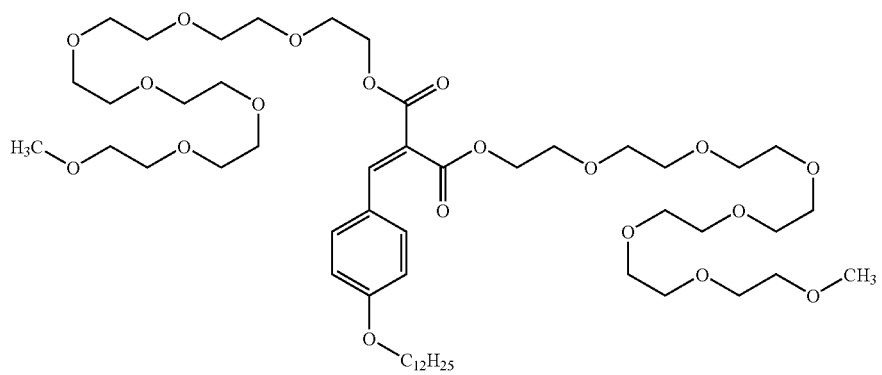

52 g of 2-(4 dodecyloxy-benzylidene)-malonic acid diethyl ester are reacted with 168 g of poly(ethylene glycol) methyl ether (Mn ca. 350), in 350 ml xylene and with 0.5 g of dibutyl tin oxide as catalyst. The reaction mixture is heated to reflux and maintained at reflux for 20 hours, at the end the dark cooled mass is washed with a 20% sodium sulphate solution and treated with 9 g of carbon. The solvent is distilled off under vacuum affording in a resinous product which gave in GPC analysis a 90% peak with a MW 1322 (polystyrene calibration).

Example A5

Preparation of 2-(4-methoxy-benzylidene)-malonic acid bis (poly(ethylene glycol) methyl ether)ester

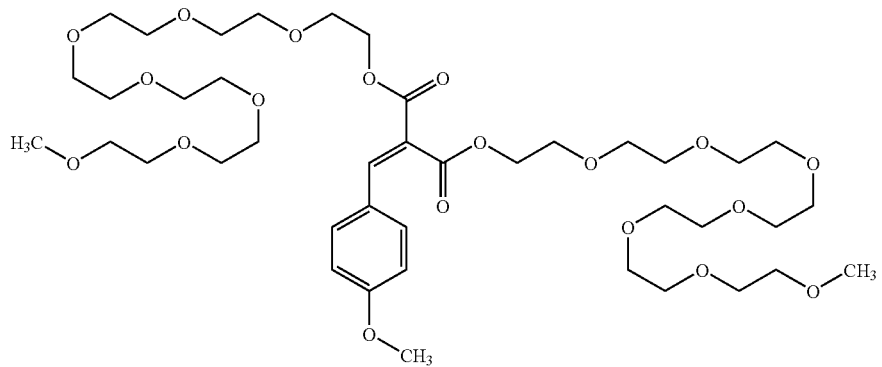

15 g of 2-(4-methoxy-benzylidene)-malonic acid diethyl ester are reacted with 75.5 g poly (ethylene glycol) methyl ether (Mn ca. 350), in 150 ml xylene and with 0.5 g of dibutyl tinoxide as catalyst for 48 hours in azeotropic reflux. At the end the dark cooled mass is washed with a 20% sodium sulphate solution to eliminate the excess of poly(ethylene glycol) methyl ether. Xylene is distilled off under vacuum and 44 g of a clear oil is collected. GPC analysis Mn 780, Mw 970.

Example A6

Preparation of 2-(4-methoxy-benzylidene)-malonic acid bis {2-(3,4 dihydroxy-tetrahydro-furan-2-yl)-2-hydroxy-ethyl}ester

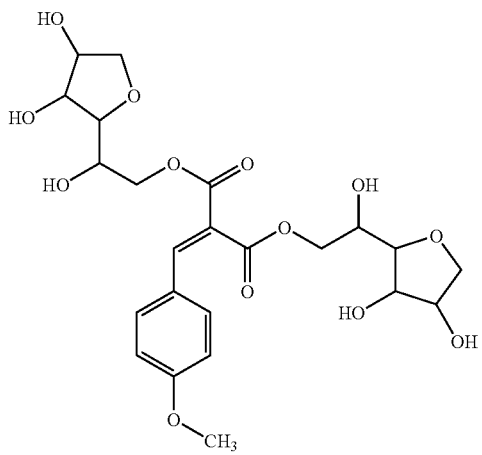

200 g of 2-(4-methoxy-benzylidene)-malonic acid diethyl ester are reacted with 295 g of sorbitane and 10 g of dibutyl tin oxide as catalyst in 500 ml of diglyme for 4 hours at reflux. The temperature is then raised up to 75-180° C. distilling off the solvent and the mixture is maintained for 10 hours at 75-180° C. At the end the residual solvent is distilled off under vacuum and the cooled reaction mass is dissolved in tert-amyl alcohol and washed with water in order to eliminate the excess of sorbitane. The solvent is distilled off under vacuum. A resinous material (220 g) solid at ambient temperature is obtained. GPC Mn 651; MW 817.

Example A7

Preparation of 2-(4-methoxy-benzylidene)malonic acid bis(2-perfluoroalkyl)ethyl ester

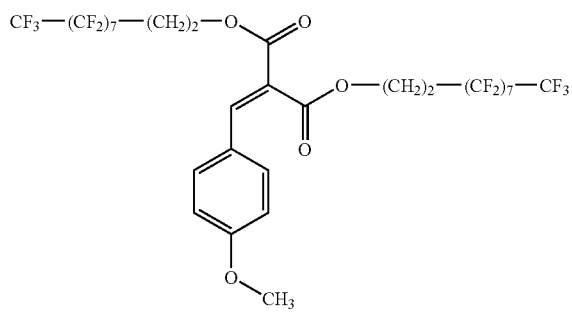

15.6 g of 2-(4-methoxy-benzylidene) malonic acid diethyl ester are reacted with 50 g of zonyl BA-L and 0.8 g of dibuthyl tin oxide as catalyst for 9 hours at 170° C., distilling off ethanol under nitrogen. The cooled reaction mass is washed with methanol in order to eliminate the unreacted zonyl. The mixture is filtered and the solid is dried under vacuum to obtain 48 g of 2-(4-methoxy-benzylidene)malonic acid bis(2-perfluoroalkyl)ethyl ester. GPC: Mn 993; Mw 1085).

Compounds of Formula II

Example A8

Preparation of cinnammylidenemalonic acid bis{2-(3,4 dihydroxy-tetrahydro-furan-2-yl)-2-hydroxy-ethyl}ester

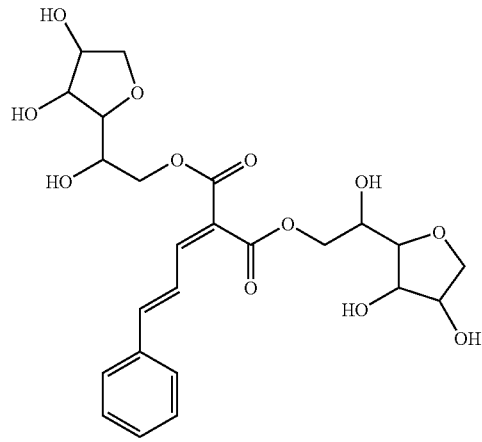

a) Preparation of diethyl cinnamylidenemalonate According to the Procedure Described in Organic Syntheses Vol. 25, page 42.

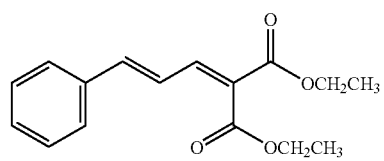

b) Preparation of the title Compound.

10 g of diethyl cinnamylidenemalonate are reacted with 17.9 g of sorbitane in 100 ml of diglyme for 48 hours at 150° C. and with 1 g of dibutyl tin oxide as catalyst. At the end the solvent is distilled off under vacuum and replaced with tert-amyl alcohol. The obtained solution is washed twice with water in order to eliminate the sorbitane excess; it is filtered and the solvent is distilled off under vacuum at 90° C. 17 g of a dark resin are obtained GPC: Mn 607; MW 820.

Example A9

Preparation of cinnammylidenemalonic acid bis(2,3 dihydroxy-propyl)ester

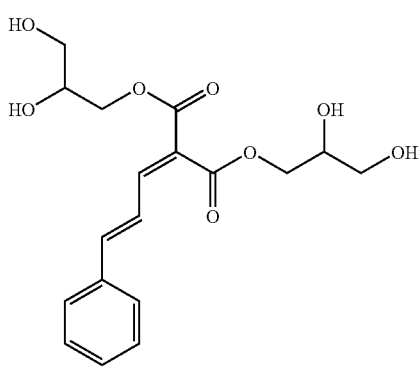

6.6 g of cinnamaldehyde and 22 g of propanedioic acid bis[(2,2-dimethyl-1,3-dioxolan-4-yl)methyl] ester are refluxed azeotropically in 100 ml of toluene with 0.5 g of piperazine as catalyst for 12 hours. The organic phase is cooled, washed with water and the solvent is distilled off. The resulting clear resin is purified through a chromatography column of silica gel using a solution hexane/THF=4/1. 11 g of di-ketal is obtained and reacted with 70 ml of absolute ethanol and 7.4 g of 6N HCl for 12 hours at ambient temperature. After distillation of the solvent under vacuum the resin is purified through a chromatography column of silica gel using a solution hexane/THF=⅕. 5.1 g of a clear resin are obtained.

Example A10

Preparation of cinnammylidenemalonic acid bis(poly(ethylene glycol) methyl ether)ester a) Preparation of diethyl cinnamylidemalonate as Described in J. Chem. Soc., Perkin Trans. 1 (1994), (10), 1267-74.

b) Preparation of the Title Compound.

20 g of diethyl cinnamylidenemalonate are reacted with 51 g of poly(ethylene glycol) methyl ether (Mn ca. 350) with 1 g of dibutyl tin oxide as catalyst at 180-90° C. under nitrogen for 5 hours. The final mixture is treated under vacuum in order to eliminate low boiling by-products and then cooled. 64 g of a dark oil are collected. GPC: Mn 1014; Mw 1140.

Example A11

Preparation of sorbitane 5-phenyl-2,4-pentadienoate

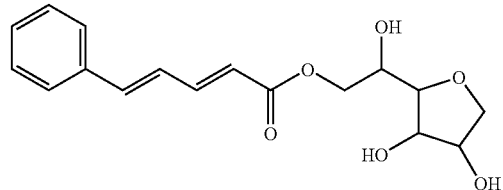

10 g of ethyl cinnamylideneacetate are reacted with 12.2 g of sorbitane in 100 ml of diglyme in presence of 1 g of dibutyl tin oxide for 48 hour at 150° C. Diglyme is distilled off under vacuum and tert-amyl alcohol is used to dissolve the reaction mass in order to wash away the excess of sorbitane. After the treatment with 1 g of carbon the solvent is distilled off. 14 g of an oil are recovered. GPC: Mn 390; Mw 1000.

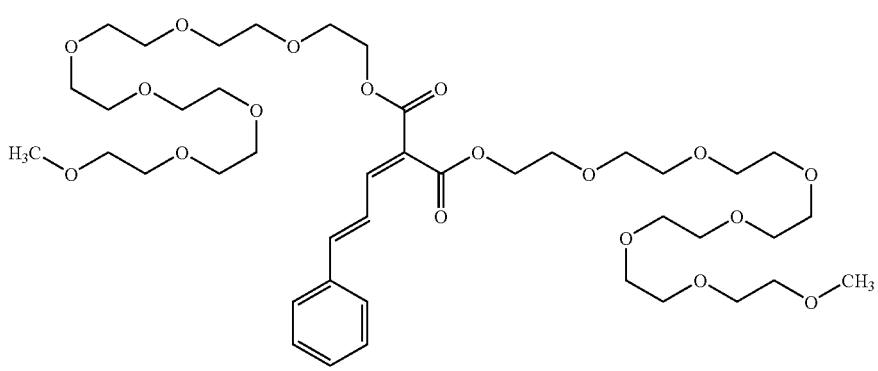

Compounds of Formula III

Example A12

Preparation of 2H-1-benzopyran-3-carboxylic acid, 2-oxo-, {2-(3,4 dihydroxy-tetrahydro-furan-2-yl)-2-hydroxy-ethyl} ester.

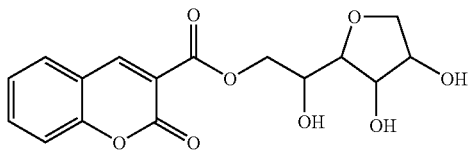

7 g of 2H-1-benzopyran-3-carboxylic acid, 2-oxo-, ethyl ester are reacted with 10.6 g of sorbitane and 0.2 g of dibutyl tin oxide as catalyst in 40 ml of diglyme for 8 hours at reflux. The reaction mixture was concentrated and dissolved in tert-amyl alcohol. The organic solution was washed three times with water and the solvent was distilled off. 6 g of a resinous product were obtained, m.p. 53-62° C. GPC Mn 502 MW 532.

Compounds of the Formula IV

Example A13

Preparation of polymer from 2-(4-methoxy-benzylidene)-malonic acid diethyl ester with triethylenglycol.

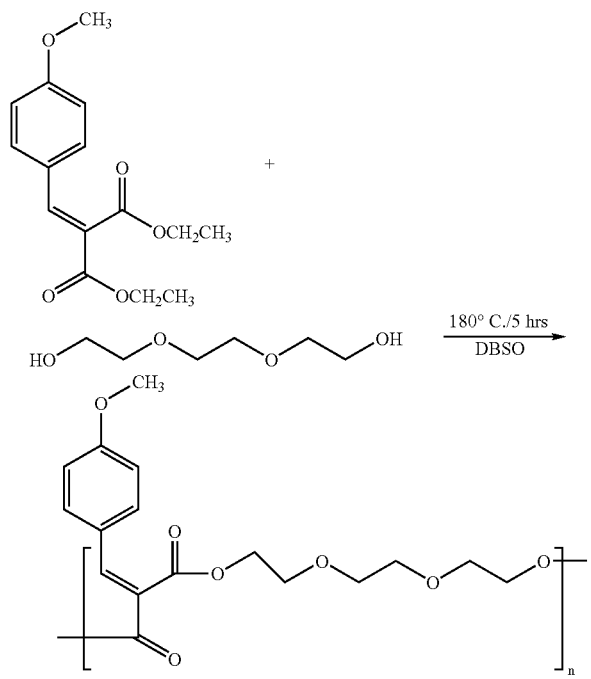

8 g (53 mmol) of triethylenglycol are refluxed azeotropically under nitrogen with 20 ml of toluene in a round-bottomed flask equipped with mechanical stirrer, a Dean-Stark apparatus, condenser and nitrogen inlet in order to eliminate trace of water. The solution is cooled to room temperature under nitrogen. Then 10 g (38 mmol) of 2-(4-methoxy-benzylidene)-malonic acid diethyl ester with 0.5 g of di-butyl tin oxide as catalyst are added and the temperature is raised up to 180° C. leaving toluene and ethanol to distill-off. The reaction is maintained for 5 hours in such conditions. The reaction mass is cooled down affording 12 g (80%) of a light brown resin. Mw 3600 (GPC PS calibration).

B: Application Examples

Example B1

Bulk Application in LDPE Films

In order to evaluate the anti-fog properties of the claimed compounds in LDPE films, they are incorporated in the polymer according to the following procedure:

Appropriate amounts of each compound are added to LDPE pellets (Riblene FF 29, supplied by Enichem, Milano, Italy), characterised by a density of 0.921 g/cm$^3$ and a melt flow index at 190° C. and 2.16 kg of 0.6, in order to obtain formulations containing 1% by weight of the compound. The formulations are mixed in a turbo mixer and extruded at a maximum temperature of 200° C. in a OMC twin-screw extruder. The granules so obtained are pressmolded in a Pasadena press for 3 minutes at 170° C., in order to obtain films of about 150 μm thickness.

Films are evaluated according a hot fog test which consists of immersing 250 ml glass beakers for about ½ of their height into a water bath at 60° C. The beakers contain about 50 ml of water and have on their top the films which have to be evaluated. Films are observed at defined intervals from the start of the experiment and a conventional notation ranging from A to E is assigned, on the basis of the appearance described in the table below.

Rating for Hot Fog Tests:

| Description | Rating | Comments |
|---|---|---|
| An opaque layer of small fog droplets | A (Bad) | Zero visibility, poor light transmission |
| An opaque layer of large droplets | B (Bad) | Zero visibility, poor light transmission |
| Complete layer of large transparent droplets | C (Poor) | Poor visibility, lens effect, dripping |
| Randomly scattered large transp. droplets | D (Fair) | Discontinuous film of water |
| Few small or large transparent droplets | D/E (Good) | Disc. water film, mostly transp. |
| A transparent film displaying no visible water | E (Excellent) | Completely transparent. |

Given the experimental conditions described, the Hot Fog Test provides a strong enhancement, though quantitatively unpredictable, of the washing off effect by water that occurs in real greenhouses.

Films containing 1% of the additives are subjected to the hot fog test immediately after their preparation. Ratings taken 2 hours after beginning of the experiment are reported below:

| Formulation | Rating |
|---|---|
| Ex. A4 | D/E after 2 hours; C after 6 hours |
| Ex. A2 | D/E after 2 hours; C after 4 hours |
| no additive | B after 2 hours, constant |

It is clear that the addition of the above compounds to the LDPE film imparts some anti-fog activity to the polymer surface. However there is a limitation for the durability of such an effect. This is due to the low amount of additive actually available on film surface. In order to force diffusion of the additive to film surface (blooming), films are exposed in a forced circulating air oven at 80° C., until some blooming occurs. Some results of the hot test performed after such treatment are reported below (additive concentration is 1% by weight).

| Formulation | Time (hrs.) at 80° C. | Performance |
|---|---|---|
| Example A2 | 2 | E rating after 1 hour, D/E after 6 hours |

The increased amount of the active compound on film surface leads to an improvement of their anti-fog performance. Yet once the bloomed additive is consumed, the effect vanishes, irrespective of the residual additive still present in the bulk of the polymer. In order to overcome the issue, a different kind of incorporation is carried out, following the procedure below.

Example B2

Surface Application

Films with no additives incorporated in the melt are prepared. To do so, LDPE pellets (same grade as in Example B1) are extruded in a semi-industrial Dolci blow-extruder at a maximum temperature of 210° C. to give films 150 μm thick. Additives are incorporated on film surface by a post-treatment consisting of spraying a solution of the additive in a proper solvent. In order to apply by spraying, about 5% solutions of the additives in a mixture of water and isopropyl alcohol (1/1 by volume) are prepared. Application by a tube-type sprayer, compressed air operated (flux approx. 20 ml/min) on a 40×40 cm square are the standard conditions. Different amounts of additives can be applied topically with the described procedure, by simply varying the volume of sprayed solution.

In the table below, additive content is 450 mg/m$^2$ (which would correspond approximately to 0.03% by weight of the same additive if incorporated in the bulk film). Performance is expressed in hours until rating D is left.

| Additive | Rating D or better (hours) |
|---|---|
| Example A2 | 120 |

A clear improvement in the time range of effectiveness of the above compounds when incorporated topically is displayed by the above data, if compared to those referring to additives incorporated during polymer processing.

Example B3

Photoreactive Surface Application

A further possibility to increase the permanency of the claimed compounds is to have them photoreacted with the polymer surface. In order to do so, sprayed films are mounted in metal frames and exposed in Atlas Ci 65 Xenon Arc Weather-O-meter, at 63° C. black panel temperature, continues dry cycle, according to ASTM G 26-96, in order to induce the photochemical reaction between the benzylidene malonate or the cinnamilidene moiety and the polyethylene macromolecules. Films are kept under irradiation for time periods in the range 100-300 hours, depending on the evolution of the reactions, followed by UV-Vis spectrophotometry (disappearance of the band of the photograftable moiety, located in the 300-350 nm range) and by FTIR spectrophotometry (shift of the carbonyl band of the ester of the photograftable moiety towards longer wavelengths, due to loss of conjugation). Films are recalled after completion of the reactions (no more changes in the above described spectra) and subjected to the hot fog test. The example below shows results of hot fog test as described in Example B1, performed after WOM exposure (450 mg/m$^2$, about 0.3% by weight):

| Additive | Rating D or better (hours) |
|---|---|
| Example A2 | 210 |

A further increase in performance durability can be observed.

Increasing the amount of additive sprayed on film surface brings about a longer lasting performance, as in the examples listed in the table below (1400 mg/m$^2$, about 1% by weight):

| Additive | Rating D or better (hours) |
|---|---|
| Example A1 | 350 |
| Example A2 | 350 |
| Example A6 | 1700 |
| Example A10 | 1700 |

In order to check the activity of the claimed compounds under real greenhouse conditions, a small experimental greenhouse is built allowing the setting up of a certain number of 30×40 cm samples, mounted on wooden frames. The experimental greenhouse contains inside wide open tanks filled with water, so that high levels of humidity are steadily reached and water condensation on the inside surface is possible. Films are periodically observed and ranked according to criteria similar to those used in the hot fog test and which are summarised below:

Rating for Experimental Greenhouse:

| Description | Perform. | Rating | Comments |
|---|---|---|---|
| An opaque layer of droplets | — | A-B | Zero visibility, dripping |
| A uniform layer of transparent droplets | Poor | C | Poor visibility, possible dripping |
| Randomly scattered transparent droplets | Fair | D | Discontinuous transp. water film |

-continued

| Description | Perform. | Rating | Comments |
|---|---|---|---|
| Rare transparent droplets | Good | D/E | Discontinuous transp. water film |
| Transparent film, no visible water | Excellent | E | Completely transparent |

Film appearance takes about 24 hours (one day+one night) to reach an equilibrium, then remains unchanged for three months, according the ratings given in the examples reported in the table below (1400 mg/m$^2$, about 1% by weight):

| Additive | Rating |
|---|---|
| Example A5 | D/E |
| Example A6 | D/E |
| no additive | A-B |

Example B4

Photoreactive Surface Application on PE Followed by Induced Photo Grafting

A different kind of pre-treatment is performed. It involves the use of a UV lamp, industrially used for photocuring of coatings. For this purpose, a 0.1% solution of the graftable compound (Ex. A2 or Ex. A9) in methanol is prepared. A low-density polyethylene blown film (PE-LD, Riblene FF29, 100 μm thick) is cut to pieces of 60×60 mm square. The solution is poured in Petri dishes, where a virgin PE film is laid. The solvent is evaporated at room temperature giving a precipitation of additive on the upper layer of the film.

The film is then irradiated to UV light using a AETEK UV processor which is equipped with two mercury middle pressure lamps (2×80 W/cm, I=400 mW/cm$^2$). The belt speed is 3 m/min. giving a exposure time of 14 seconds per cycle. The PE film is exposed up to five cycles. The PE film is immersed in isopropanol for one hour at room temperature to remove ungrafted material on the surface. The film is dried at room temperature.

The PE film is then characterised using a Krüss Processor Tensiometer K12. A 50×25 mm sample is measured using the Wilhelmy method and water as measuring liquid. This method can satisfactorily be used, although only one side of the film is covered with a grafted layer. The difference in the advancing and receding contact angles compared to a blank sample give the indication if a grafting reaction occurred during the irradiation. The surface tension of the water used for the contact angle measurement show if impurities or unreacted material is dissolved in the water during the contact angle measurement. In this case the surface tension is below 70 mN/m.

TABLE 1

Advancing and receding contact angles and surface tensions of the used water.

| Polymer | Additive | Adv. Contact Angle [°] | Rec. Contact Angle [°] | Surf. Tens. [mN/m] |
|---|---|---|---|---|
| PE-LD | Ex. A2 | 103 | 50 | 72.0 |
| PE-LD | Ex. A9 | 90 | 56 | 66.4 |
| PE-LD | blank | 90 | 63 | 71.7 |

The polymer surface is also observed by scanning electron microscopy. A Philips scanning electron microscope SEM 525 M is used. The acceleration voltage is 10 kV. The films are examined and micrographs are taken with a magnification between 500× and 2000×. The UV exposed samples show a thin layer on the polymer surface.

Example B5

Photoreactive Surface Application on PP Followed by Induced Photo Grafting

The procedures are the same as in Example B4 but polypropylene injection molded plaques (PP, Profax 6501, 60×60×1 mm) are used instead of the PE films.

TABLE 2

Advancing and receding contact angles and surface tensions of the used water.

| Polymer | Additive | Adv. Contact Angle [°] | Rec. Contact Angle [°] | Surf. Tens. [mN/m] |
|---|---|---|---|---|
| PP | Ex. A2 | 99 | 57 | 72.5 |
| PP | Ex. A9 | 92 | 48 | 70.0 |
| PP | blank | 95 | 71 | 72.4 |

Example B6

Photoreactive Surface Application on PC Followed by Induced Photo Grafting

The procedures are the same as in Example B4 but polycarbonate injection molded plaques (PC, Lexan 141R, 60×60×2 mm) are used instead of the PE films and the UV irradiation is made using an UV exposure chamber with 2 UV lamps of 15 W (chamber is manufactured by Ted Pella Inc., Redding Calif.) instead of the AETEK UV processor. The exposure time is 24 hours.

TABLE 3

Advancing and receding contact angles and surface tensions of the used water.

| Polymer | Additive | Adv. Contact Angle [°] | Rec. Contact Angle [°] | Surf. Tens. [mN/m] |
|---|---|---|---|---|
| PC | Ex. A2 | 74 | 0 | 72.5 |
| PC | blank | 85 | 44 | 72.7 |

Example B7

Photoreactive Surface Application on PET Followed by Induced Photo Grafting

The procedures are the same as in Example B4 but polyethylene-terephthalate (PET) injection molded plaques (PET, Arnite D04 300, 60×60×2 mm) are used instead of the PE films and the UV irradiation was made using an UV exposure chamber with 2 UV lamps of 15 W (chamber is manufactured by Ted Pella Inc., Redding Calif.) instead of the AETEK UV processor. The exposure time is 24 hours.

TABLE 4

Advancing and receding contact angles and surface tensions of the used water.

| Polymer | Additive | Adv. Contact Angle [°] | Rec. Contact Angle [°] | Surf. Tens. [mN/m] |
|---|---|---|---|---|
| PET | Ex. A2 | 76 | 0 | 72.6 |
| PET | blank | 68 | 33 | 72.6 |

Example B8

Water Repellency in LDPE Films

In order to characterize the surface properties imparted by the compounds of the formula I, II, III or IV, proper amounts of it are mixed with LDPE pellets (Riblene FF 29, supplied by Polimeri Europa, Milano, Italy), characterized by a density of 0.921 g/cm$^3$ and a melt flow index at 190° C. and 2.16 kg of 0.6 in a turbo mixer in order to give the formulations containing the additives. The mixtures are extruded at a maximum temperature of 200° C. in a OMC twin-screw extruder. The granules so obtained are blown in a semi-industrial scale Dolci blow-extruder at a maximum temperature of 210° C. to give films of 150 μm thickness. The films are analyzed by means of a Kruess Processor Tensiometer K12: The advancing and receding contact angles are measured using the Wilhelmy plate method and employing 17×15 mm specimen. Results on freshly prepared films are summarized in Table 5.

TABLE 5

| Polymer | % wt. additive | Adv. Contact angle (°) | Rec. contact angle (°) |
|---|---|---|---|
| LDPE | Blank | 105 | 85 |
| LDPE | 0.5% Ex. A7 | 108 | 89 |
| LDPE | 1.0% Ex. A7 | 109 | 89 |
| LDPE | 2.0% Ex. A7 | 104 | 89 |

A slight increase of contact angles as compared to the blank sample indicates that, due to fluorine in proximity of the surface, polymer hydrophobicity increases. In order to increase the permanency of the claimed compounds they are photoreacted by mounting in metal frames and exposing them into an Atlas Ci 65 Xenon Arc Weather-O-meter (WOM), at 63° C. black panel temperature, continuous dry cycle, according to ASTM G 26-96, in order to induce the photochemical reaction between the benzylidenemalonate and the polyethylene macromolecules. Films are kept into the WOM for about 250 hours, that are known to induce in such conditions the complete reaction of the benzylidenemalonate moiety. The contact angle measurements were repeated on the exposed samples and the results are reported in Table 6.

TABLE 6

| Polymer | % wt. additive | Adv. Contact angle (°) | Rec. contact angle (°) |
|---|---|---|---|
| LDPE | Blank | 100 | 73 |
| LDPE | 0.5% Ex. A7 | 117 | 77 |
| LDPE | 1.0% Ex. A7 | 123 | 77 |
| LDPE | 2.0% Ex. A7 | 120 | 77 |

As expected, contact angle values in the blank film decrease, due to the oxidation onset of the polymer surface, that renders it more hydrophilic. Quite unexpectedly, the advancing contact angle—the most representative value in the case of a low surface tension surface as is the case of LDPE—definitely increases, as compared to the corresponding advancing contact angle values of the non exposed films.

Surface tension of the water used for contact angle measurements is also determined. The results are summarized in Table 7.

TABLE 7

| Polymer | % wt. additive | Surface Tension (mN/m) |
|---|---|---|
| LDPE, non irradiated | 2.0% Ex. A7 | 57.2 |
| LDPE, irradiated | 2.0% Ex. A7 | 71.4 |

Example B9

Water Repellency in PP Plaques

A proper amount of a compound of the formula I, II, III or IV, 0.33 g of tris(2,4-di-ter-butyl-phenyl)phosphite, 0.17 g of pentaerythritol tetrakis (3-(3,5-di-tert-butyl-4-hydroxyphenyl)propionate) and 1 g of calcium stearate are mixed in a turbomixer with 1000 g of polypropylene powder (JE 6100, supplied by Basell, Ferrara, Italy, having a melt index of 2.0, measured at 230° C. and 2.16 kg). The mixture is extruded at 200-230° C. to give polymer granules which are subsequently converted to plaques of 2 mm thickness, using an injection molding machine (Negribossi—Italy) and working at a maximum temperature of 220° C. The plaques are exposed into the WOM, then analyzed as regards the water contact angle on their surface, using the same experimental set up described for LDPE films (Example B8). The results obtained on plaques exposed to light for 250 hours are summarized in Table 8.

TABLE 8

| Polymer | % wt. additive | Adv. Contact angle (°) | Rec. contact angle (°) |
|---|---|---|---|
| PP | Blank | 94 | 69 |
| PP | 1.0% Ex. A7 | 107 | 79 |
| PP | 2.0% Ex. A7 | 110 | 72 |

Example B10

Water Repellency; Topical Application in PP Nonwovens

An industrial sample of polypropylene nonwoven is dipped into a 0.25% or 2% isopropanol solution of a compound of the formula I, II, III or IV, simultaneously subdued to ultrasonic energy for 5 minutes. After that, the samples are dried overnight at room temperature, then 2 hours at 90° C. and 10 minutes at 130° C. Finally samples are exposed to UV light using a AETEK UV processor (belt speed 10 m/min, 10 cycles, total exposure time 21 seconds). A water repellency test (INDA IST 80.9), consisting in the observation of the wetting behavior of a series of water/isopropanol mixtures and rating the result from 0 (water wetting, no repellency) to 10 (optimum water repellency) is performed on the so treated specimens. The results are summarized in Table 9.

TABLE 9

| Solution conc. In isopropanol | UV exposure | Rating |
| --- | --- | --- |
| Blank | No | 2 |
| 0.25% Example A7 | No | 8 |
| 0.25% Example A7 | Yes | 7 |
| 2.0% Example A7 | No | 7 |
| 2.0% Example A7 | Yes | 8 |

Example B11

Oil Repellency in LDPE Films

The contact angles measurements described before on LDPE films (Example B8) are performed also using as a solvent diiodomethane, in order to apply the Wu method for the calculation of the surface tension of the polymer. The results are summarized in Table 10.

TABLE 10

| % wt. additive | WOM exposure | Surface Tension (mN/m) |
| --- | --- | --- |
| Blank | No | 30.6 |
| Blank | Yes | 30.8 |
| 0.2% Example A7 | Yes | 16.5 |
| 2.0% Example A7 | Yes | 13.5 |

The marked decrease in the surface tension values of light irradiated samples containing a compound according to the instant invention with respect to blank LDPE and non exposed sample indicate that, upon exposure to UV light, the polymer surface has become repellent to apolar liquids, such as hydrocarbons and oils in general.

Example B12

Oil Repellency; Topical Application in PP Nonwovens

The samples subjected to the same treatments for testing their water repellency (see Example B10) are tested also in terms of oil repellency through a hydrocarbon resistance test (AATCC 118/1997, ISO 14419). This test follows the same concepts of the already described water repellency test method, but using, as testing solvents, a series of hydrocarbons. Also in this case rating goes from 0 (no repellency) to 10 (maximum repellency). The results are summarized in Table 11.

TABLE 11

| Solution conc. In isopropanol | UV exposure | Rating |
| --- | --- | --- |
| Blank | No | 0 |
| 0.25% Example A7 | No | 5 |
| 0.25% Example A7 | Yes | 5 |
| 2.0% Example A7 | No | 6 |
| 2.0% Example A7 | yes | 6 |

What is claimed is:

1. A composition comprising
a) a polymer or a mixture of polymers and
b) as additive for surface modification, at least one compound of the formula I or II or sorbitane 5-phenyl-2,4-pentadienoate, or a mixture thereof;

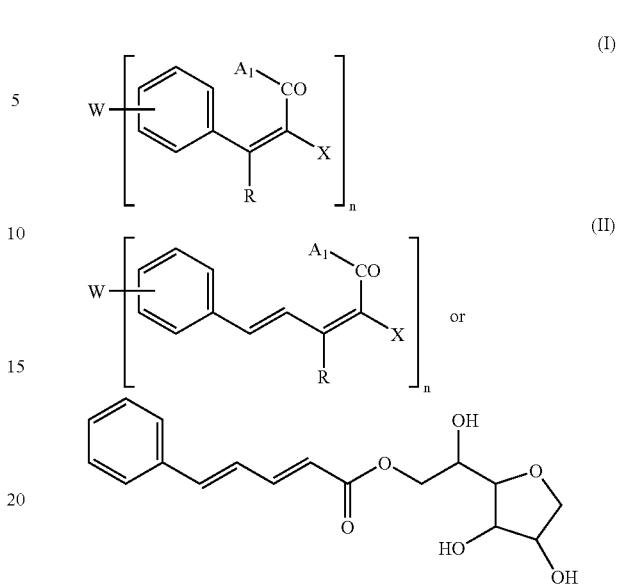

sorbitane 5-phenyl-2,4-pentadienoate wherein $A_1$ is a polyoxyalkylene ether residue of the formula
—O—[—$CH_2$—$CH_2$—O]$_q$—$CH_2$—$CH_2$—$OR_2$, wherein q is from 4 to 30 and $R_2$ is $C_1$-$C_{20}$alkyl,;
—O—$CH_2$—$CH_2$—($CF_2$)$_j$—$CF_3$, wherein j is from 3 to 8; a glycerol residue or a sorbitane residue, X is —C(O)$A_1$, R is hydrogen, W is hydrogen or $C_1$-$C_{20}$alkoxy and n is 1.

2. A composition according to claim 1, wherein the polymer is a polyolefin, a polyester or a polycarbonate.

3. A composition according to claim 1, wherein component (b) is present in an amount of from 0.01 to 10% based on the weight of component (a).

4. A composition according to claim 1, wherein the polymer or mixture of polymers is in the form of a film or a sheet.

5. A process for modifying the surface of polymers in order to improve resistance to fog formation or water and oil repellency, which comprises incorporating therein or applying thereto at least a compound of the formula I or II or sorbitane 5-phenyl-2,4-pentadienoate;

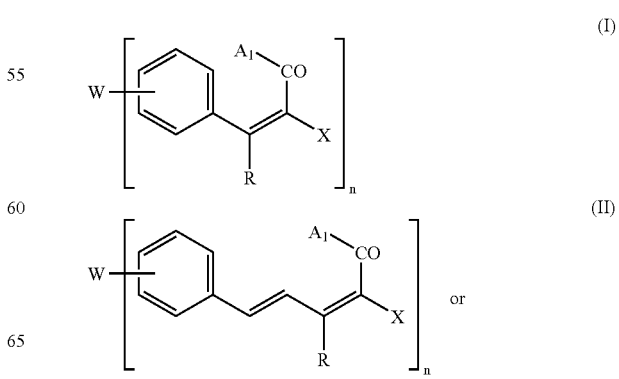

-continued
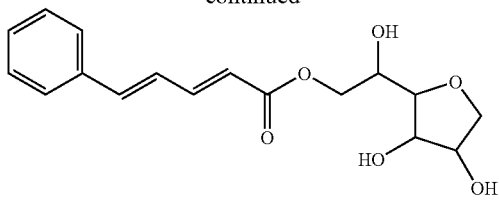
sorbitane 5-phenyl-2,4-pentadienoate
wherein
$A_1$ is a polyoxyalkylene ether residue of the formula
—O—[—CH$_2$—CH$_2$—O]$_q$—CH$_2$—CH$_2$—OR$_2$,
wherein q is from 4 to 30 and $R_2$ is $C_1$-$C_{20}$alkyl,;
—O—CH$_2$—CH$_2$—(CF$_2$)$_j$—CF$_3$, wherein j is from 3 to 8; a glycerol residue or a sorbitane residue,
X is —C(O)A$_1$,
R is hydrogen,
W is hydrogen or $C_1$-$C_{20}$alkoxy and
n is 1.
* * * * *